United States Patent [19]

Bennett

[11] Patent Number: Plant 5,380

[45] Date of Patent: Jan. 1, 1985

[54] LITTLE AMIGO

[76] Inventor: Cecilia L. D. Bennett, 489 Minot Ave., Chula Vista, Calif. 92010

[21] Appl. No.: 521,343

[22] Filed: Aug. 8, 1983

[51] Int. Cl.[3] ..... A01H 5/00

[52] U.S. Cl. ..... Plt./10

[58] Field of Search ..... Plt./10

*Primary Examiner*—Robert E. Bagwill

[57] ABSTRACT

The subject of the present disclosure is a new and distinct variety of miniature rose plant, named 'Little Amigo', which is characterized by its blooms of intense Vermilion and vigorous growth habit. (More detailed description to follow.)

1 Drawing Figure

The present invention relates to a new and distinct variety of a hardy, dwarf, miniature bush plant of the miniature class; the variety being primarily characterized as an orange-red.

The variety is further characterized by:

Long stemmed blooms, borne singly or in sprays, held very erect and well above the foliage.

Has a slight fragrance.

The plant ranges in height from 12 to 24 inches. The canes are sturdy and erect, heavily branched with medium foliage covering. The plant is a moderate to heavy bloomer that does well in either the green house or outdoors.

The plant is very vigorous with good growth habits, well shaped and attractive in appearance, bearing numerous leaflets of average size.

The seed parent was Futura (U.S. Plant Pat. No. 3,569), and the pollen parent was Orange Honey (Miniature Rose Plant, orange blend; R. S. Moore; introduced by Sequoia Nursery, 1979).

Subsequent to the origination of the variety, I have successfully reproduced it at Tiny Petals Nursery located at aforesaid retaining the distinguishing characteristics through succeeding propagations by cuttings.

The descriptive matter which follows pertains to roses grown and color values observed in plants and newly opened blooms in the months of July and August. The plants were grown outdoors in Chula Vista, Calif., and are believed to be accurate standards for this same cultivar in similar conditions of soil and climate elsewhere.

The color photograph illustrates the variety.

Referring now specifically to the new and distinct variety of miniature rose plant named 'Little Amigo', the following is a detailed description thereof in outline; all major color plate identifications being by reference to The British Colour Council Horticultural Colour Chart, except where common terms of color definition are employed.

Type: Hardy, dwarf, bushy, green house or outdoor, exhibition quality or garden decoration potted plant.

Class: Miniature.

Variety name: Little Amigo.

Flowers borne: One to a stem or in sprays of 3 to 5 or more on erect stems with foliage well below the blooms.

Quantity of bloom: Moderate to heavy both outdoors and greenhouse grown.

Bud:

*Peduncle.*—Medium to long (averaging 25 to 30 mm); average diameter and sturdy; medium green with light to occasionally heavy tinting of bronze.

*Hairs.*—Extremely small and abundant over the entire surface of the peduncle, calyx tube and sepals.

*Calyx.*—Color is near Pod Green (061 to 061/1 page 120).

*Opening.*—Opens well in all weather.

Bloom:

*Size when fully open.*—Average for a miniature variety (35 to 40 mm).

*Petalage.*—Double — Averaging about 30 to 40 petals, arranged regularly plus petaloids (6 to 10 or more).

*Form.*—Urn-shaped to ovoid as the bloom progresses. The petals remain at first somewhat tightly cupped with the tips and/or margins reflexed outward, becoming later at maturity more loosely cupped. At the fully open stage, the petals reflex at their margins, rolling under from the apex petal on of the petals on both sides.

Petals: Fairly thick with good substance and a matte finish.

*Shape.*—Outer petals are of a broad obovate form with a slight peak at the apex. The intermediate petals are very much like the outer petals only narrower. The inner petals are narrower obovate form; very little difference between the intermediate and inner petals in noticeable. The petaloids are like small lanceolates with occasional irregularities in shape.

Color: Newly opened flowers from plants grown outdoors (July and August 1983), Chula Vista, Calif.

*All petals and petaloids.*—Upper surfaces — Near Vermilion (18 to 18/1 page 18) with a small area at the base of the petal of white to near white. Under surfaces — Near Geranium Lake (20 to 20/1 page 20) with a small area at the base of the petal of Geranium Lake (20/2 to 20/3 page 20) and a very small base tip of white to near white.

*Flower longevity.*—(July and August 1983) Plant in pot 4 to 6 days from bud with sepals down to fully open bloom. Holding at fully open with barely any noticeable fading of color for additional 6 to 8 days before dropping petals. Cut blooms at livingroom temperature 4 to 5 days or longer from bud to open bloom.

Reproductive ogans:

*Stamens.*—A generous amount arranged uniformly around the pistil.

*Filament.*—Varying in length; reddish in color.

*Pollen.*—Abundant.

*Pistol.*—Short, abundant and compacted together by stamens.

*Styles.*—Short and uniform in length; reddish in color.

*Ovaries.*—All encased in calyx.

*Hips.*—Some.

*Seed.*—Few or none.

*Sepals.*—Permanent; spear-shaped; open as bloom opens, but does not recurve against the peduncle.

Foliage:

*Leaves.*—Five to seven leaflets on the average; medium size for a miniature rose plant.

*Leaflets.*—Broad ovate-shaped.

*Margin.*—Very serrated with occasional tinting of bronze.

*Color.*—Ranging from near Scheeles Green (860 to 860/1 page 175) to near Spinach Green (0960 to 0960/1 page 187) with occasional bronzing of the margins. The upper surface have a satiny finish, and the under surfaces have a matte finish of a slightly lighter shade than the upper surfaces.

*Rachis.*—Medium strength; upper surface may have a few small hair; grooved. Under side is smooth except for a few sparse thorns.

*Stipules.*—Varying in length from short to medium; average width; tapering auricles angled outward at about 45 degrees.

Growth:

*Habit.*—Dwarf, bushy, much branched; average to large for a miniature rose plant.

*Growth.*—Vigorous.

*Canes.*—Medium; sturdy; held very erect.

*Main stems.*—Color — Ranging from near Scheeles Green (860 to 860/1 page 175) to near Spinach Green (0960 to 0960/1 page 187) with occasional tinting of bronze, especially noticeable on the newer stems.

*Thorns.*—Averaging 12 to 15 per 10 cm on the main stems, and fewer on the branches. Pale yellow or reddish in color with occasional bronzing. Average to large in size. May be straight or hooked slightly downward.

*Branches.*—Color — Ranging from near Scheeles Green (860 to 860/1 page 175) to near Spinach Green (0960 to 0960/1 page 187) with occasional bronzing. Thorns — As previously described. Prickles — Some on the smaller branches only. Hairs — None.

The miniature rose plant and its flowers as herein described may vary in slight detail due to climatic, soil and cultural conditions under which the variety may be grown; the present description being of the variety as grown at Chula Vista, Calif.

The following is claimed:

1. A new and distinct variety of miniature rose plant named 'Little Amigo' of hardy, dwarf, bushy, much branched habit, substantially as illustrated and described, characterized by its blooms of intense Vermilion and vigorous growth habit, easy to propagate from cuttings, with flower usually borne singly or in sprays of 3 to 5 or more.

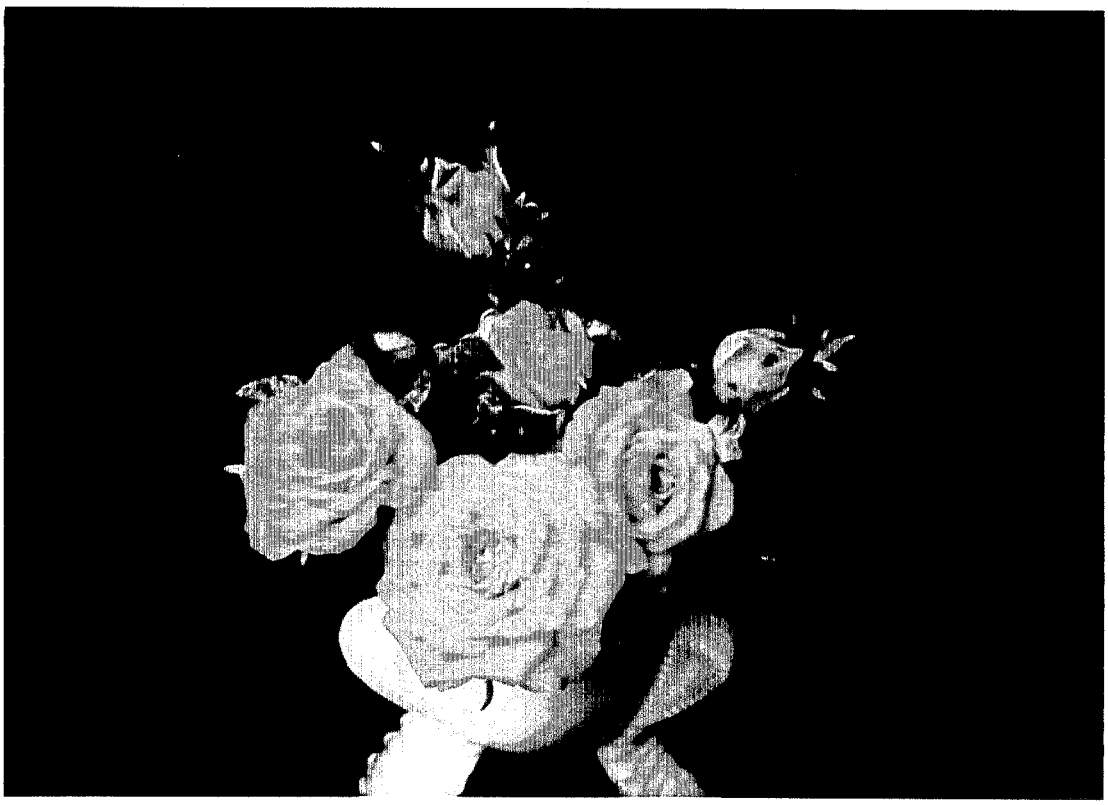

* * * * *